United States Patent
Rowland et al.

[11] Patent Number: 5,868,698
[45] Date of Patent: Feb. 9, 1999

[54] APPARATUS FOR PERFORMING DIAGNOSTIC AND THERAPEUTIC MODALITIES IN THE BILIARY TREE

[75] Inventors: Christopher A. Rowland, Marlborough, Mass.; Michael G. Vergano, Cumberland, R.I.; Bryan P. Eddy, North Graften, Mass.; Peter B. Cotton, Durham, N.C.

[73] Assignee: Boston Scientific Corporation, Watertown, Mass.

[21] Appl. No.: 842,210

[22] Filed: Apr. 23, 1997

Related U.S. Application Data

[63] Continuation of Ser. No. 648,356, May 14, 1996, Pat. No. 5,683,362, which is a continuation of Ser. No. 242,168, May 13, 1994, Pat. No. 5,547,469.

[51] Int. Cl.$^6$ ................................................. A61B 17/22
[52] U.S. Cl. ............................... 604/22; 604/96; 606/159
[58] Field of Search .............................. 604/22, 49, 53, 604/54, 96, 100, 101, 280, 282; 606/159, 167, 170, 192–194

[56] References Cited

U.S. PATENT DOCUMENTS

| | | | |
|---|---|---|---|
| 518,600 | 4/1894 | Hallman . | |
| 2,715,899 | 4/1955 | MacLean | 128/2 |
| 2,854,983 | 10/1958 | Baskin | 604/96 |
| 3,108,593 | 10/1963 | Glassman | 128/328 |
| 4,271,839 | 6/1981 | Fogarty et al. | 128/344 |
| 4,273,128 | 6/1981 | Lary | 606/159 |
| 4,295,464 | 10/1981 | Shihata | 128/1 |
| 4,484,579 | 11/1984 | Meno et al. | 128/305 |
| 4,561,439 | 12/1985 | Bishop et al. | 128/348 |
| 4,627,837 | 12/1986 | Gonzalo | 604/101 |
| 4,690,138 | 9/1987 | Heyden | 128/207 |
| 4,696,668 | 9/1987 | Wilcox | 604/28 |
| 4,705,041 | 11/1987 | Kim | 128/343 |
| 4,734,094 | 3/1988 | Jacob et al. | 604/284 |
| 4,758,221 | 7/1988 | Jureidini | 604/95 |
| 4,781,677 | 11/1988 | Wilcox | 604/28 |
| 4,798,586 | 1/1989 | Stevens | 604/4 |
| 4,811,735 | 3/1989 | Nash et al. | 128/305 |
| 4,813,930 | 3/1989 | Elliott | 604/53 |
| 4,909,781 | 3/1990 | Husted | 604/22 |
| 4,911,163 | 3/1990 | Fina | 606/127 |
| 4,979,951 | 12/1990 | Simpson . | |
| 5,024,617 | 6/1991 | Karpiel | 128/772 |
| 5,035,696 | 7/1991 | Rydell | 606/47 |
| 5,053,044 | 10/1991 | Mueller et al. | 606/159 |
| 5,078,722 | 1/1992 | Stevens | 606/159 |
| 5,087,265 | 2/1992 | Summers | 606/159 |
| 5,152,771 | 10/1992 | Sabbaghian et al. | 606/159 |
| 5,152,772 | 10/1992 | Sewell, Jr. | 606/159 |
| 5,181,920 | 1/1993 | Mueller et al. | 606/159 |
| 5,195,955 | 3/1993 | Don Michael | 604/22 |
| 5,250,060 | 10/1993 | Carbo et al. | 604/159 |
| 5,395,311 | 3/1995 | Andrews | 604/22 |
| 5,547,469 | 8/1996 | Rowland | 604/22 |

FOREIGN PATENT DOCUMENTS

| | | | |
|---|---|---|---|
| 0 359 447 | 3/1990 | European Pat. Off. . | |
| 0 385 588 | 9/1990 | European Pat. Off. . | |
| 1 355 266 | 11/1987 | U.S.S.R. | 606/159 |
| 9 117 714 | 11/1991 | WIPO | 606/159 |
| 92/12762 | 8/1992 | WIPO . | |

OTHER PUBLICATIONS

Patent Abstracts of Japan,, Appln. No. 04101111, Appln. Date Apr. 21, 1992.

*Primary Examiner*—John D. Yasko
*Attorney, Agent, or Firm*—Finnegan, Henderson, Farabow, Garrett & Dunner, L.L.P.

[57] ABSTRACT

Catheter apparatus for performing diagnostic and therapeutic modalities in the biliary tree includes a catheter with multiple lumens. A first lumen is adapted to receive a guidewire and can serve as a transport lumen for contrast agent. A second lumen carries a cutting wire for performing a sphincterotomy. A third lumen can be used as an inflation lumen for a distally located balloon. Expansion of the balloon occludes a portion of the biliary tree and allows the catheter to sweep any gallstones through the sphincter of Oddi into the duodenum.

35 Claims, 5 Drawing Sheets

APPARATUS FOR PERFORMING DIAGNOSTIC AND THERAPEUTIC MODALITIES IN THE BILIARY TREE

CROSS REFERENCE TO RELATED APPLICATION

This is a continuation application of our co-pending U.S. patent application Ser. No. 08/648,356 filed May 14, 1996 now U.S Pat. No. 5,683,362 for an Apparatus for Performing Diagnostic and Therapeutic Modalities in the Biliary Tree that is a continuation of our U. S. patent application Ser. No. 08/242,168 filed May 13, 1994 for an Apparatus for Performing Diagnostic and Therapeutic Modalities in the Biliary Tree now U.S. Pat. No. 5,547,469 issued Aug. 20, 1996.

BACKGROUND OF THE INVENTION

1. Field of the Invention

This invention generally relates to apparatus that is useful in performing diagnostic and therapeutic modalities in the biliary tree and more particularly to apparatus that is adapted for facilitating the diagnosis of gallstones in the bile duct and other portions of the biliary tree and the removal of such gallstones.

2. Description of Related Art

Historically the migration of gallstones into an individual's common bile duct was corrected by general surgical procedures. A surgeon would incise the bile duct and remove the gallstones and normally remove the gallbladder. In recent years less invasive treatment modalities have replaced these general surgical procedures and reduced patient trauma, long hospital stays and recovery periods.

For example, U.S. Pat. No. 4,696,668 and U.S. Pat. No. 4,781,677, both to Wilcox, disclose a treatment modality involving the administration of a dissolution agent in the bile duct to essentially dissolve any gallstones. More specifically, a catheter contains several lumens for inflating and deflating each of two balloons, venting bile, and infusing and aspirating the dissolution agent. Inflating the balloons occludes the bile duct at two spaced sites and creates a sealed spaced that receives the dissolution agent. As the space is sealed from the remaining biliary tree, the dissolution agent finds access to the gallbladder and any gallstones therein through the cystic duct with the exclusion of bile from the gallbladder fundus. The dissolution agent also will be confined in high concentration around bile duct gallstones. After the gallstones dissolve the balloons are deflated and the catheter can be withdrawn. In this particular approach, the catheter is directed into the biliary tree using a standard duodenoscope that passes through the alimentary tract. Although this and analogous approaches have the potential of minimizing patient trauma, such treatments require extended placement of the duodenoscope in the patient, exhibit low efficacy and introduce a potential for adverse reactions to the dissolution agents.

In an alternative approach, a surgeon directs a surgical extractor into the biliary tree through at least an incision in the bile duct. For example, in U.S. Pat. No. 3,108,593 to Glassman a surgeon incises both the bile duct and duodenum. Then the surgeon directs an extractor through the bile duct incision, biliary tree, sphincter of Oddi and duodenum to exit through the duodenum incision. This extractor includes a series of longitudinally spaced cages for trapping any gallstones in the bile duct and removing them through either of the incisions.

U.S. Pat. No. 4,627,837 to Gonzalo discloses a catheter device with a pair of inflatable balloons at its distal end. This catheter is led through an incision in the bile duct toward the duodenum. After the distal balloon passes through the sphincter of Oddi, both balloons are expanded to anchor the catheter in place. This enables the catheter to be used for irrigating and flushing through other lumens in order to capture any gallstone in the second balloon for removal through the incised bile duct.

In accordance with still another modality as for the treatment of strictures, a surgeon may insert a catheter device through the bile duct or duodenum for the purpose of dilating or enlarging the sphincter of Oddi. For example, U.S. Pat. No. 4,705,041 to Kim discloses a dilator that is directed through an incision in the bile duct and the sphincter of Oddi. An expandable tip dilates the sphincter of Oddi. U.S. Pat. No. 5,035,696 to Rydell discloses an electrosurgical instrument that is directed through the duodenum and to the sphincter of Oddi for performing a sphincterotomy. This apparatus contains a cutting wire that is heated to cut the sphincter muscle. U.S. Pat. No. 5,024,617 to Karpiel, discloses a similar device that can be directed through a duodenoscope. U.S. Pat. No. 5,152,772 to Sewell, Jr. discloses a device for performing a sphincterotomy that is directed through an incision in the bile duct and includes a knife for cutting the sphincter muscle.

The use of the duodenoscope and sphincterotomy devices, such as shown in the Rydell and Karpiel patents, enables an internist to diagnose and treat problems in the biliary tree with minimal patient invasion. For example, modalities as described in these patents eliminates the surgery needed for incising the bile duct. Consequently, these modalities can be performed as outpatient or day surgical procedures. These procedures greatly reduce patient trauma, the length of a hospital stay and recovery times. For example, if an internist determines that gallstones are present in the biliary tree, particularly the common bile duct, the internist can insert a duodenoscope into the duodenum to view the sphincter of Oddi. Then a first catheter can be advanced through the working channel of the duodenoscope with or without a guidewire and directed through the sphincter of Oddi into the biliary tree. Contrast agent injected through the catheter enables fluoroscopy or other imaging procedures to confirm the presence of gallstones within the biliary tree. Next the internist exchanges the first catheter for a second catheter for performing a sphincterotomy such as the types disclosed in the above-identified Rydell and Karpiel patents. The second catheter is then exchanged for a third catheter such as shown in the Glassman patent or some other equivalent retrieval catheter for drawings gallstones through the enlarged sphincter of Oddi. Thereafter the retrieval catheter is manipulated to release the gallstone into the duodenum. The catheter, any guidewire and the duodenoscope can then be removed to complete the procedure.

This procedure is significantly less traumatic to the patient than other prior art procedures because the only incision occurs during the sphincterotomy. However, this procedure as presently practiced requires three separate catheters and two catheter exchanges. These exchanges are required because the first, second and third catheters function solely to inject contrast agent to perform the sphincterotomy and to dislodge gallstones, respectively. The time required for performing each catheter exchange can increase patient trauma and increase the duration of the procedure and reduce efficiency. Moreover, each such procedure requires the use of two or three separate catheter devices.

SUMMARY

Therefore, an object of this invention is to provide apparatus for performing both diagnosis and additional therapeutic treatment without requiring a catheter exchange.

Another object of this invention is to provide apparatus for performing diagnosis and treatment in the biliary tree that can reduce patient trauma.

Yet another object of this invention is to provide apparatus that enables the removal of gallstones from the biliary tree by a procedure that reduces the number of required catheters and catheter exchanges.

Still another object of this invention is to provide a single catheter apparatus that can perform a sphincterotomy and remove gallstones in the common bile duct.

Yet another object of this invention is to provide a single catheter apparatus that can perform a sphincterotomy and inject contrast material into the biliary tree.

Still yet another object of this invention is to provide a single catheter apparatus that can inject contrast agent into biliary tree, performing a sphincterotomy and remove gallstones in the bile duct into the duodenum.

In accordance with one aspect of this invention, apparatus can be used in a treatment modality including an enlargement procedure and another procedure to be performed. This apparatus includes a catheter with proximal and distal ends and proximal and distal portions. The catheter includes first, second and third generally parallel lumens. The first lumen has a greater diameter than either of the second and third lumens and the lumens each extend between proximal and distal portions of the catheter. The apparatus for performing the enlargement procedure extends through the second lumen for operating distally of the catheter in response to manipulations of an operator at the proximal end of the catheter. The first lumen has a proximal port for enabling access to the first lumen and the third lumen has a proximal port and a distal port for enabling the remote control of some other procedure.

In accordance with another aspect of this invention, apparatus is provided for removing objects from the biliary tree. This apparatus includes a catheter that is directed through the working channel of a duodenoscope and the sphincter of Oddi into the biliary tree. The catheter includes first, second and third lumens with the first lumen being larger than either the second or third lumens and the lumens generally extending between proximal and distal portions of the catheter along parallel axes. Apparatus for cutting the sphincter of Oddi includes a cutting wire extending through the second lumen and externally of the catheter means through a distal port along a length that is coextensive with part of the distal portion of the catheter. A handle attaches to the catheter at the proximal portion and to the proximal wire portion to control the position and orientation of the cutting wire. An expansible balloon is mounted on the distal portion spaced from the cutting wire and can be inflated through the third lumen in order to move any gallstone in the biliary tree through the enlarged sphincter of Oddi.

In accordance with still another aspect of this invention, the apparatus is provided for directing contrast agent into the biliary tree and performing a sphincterotomy through the working channel of a duodenoscope. This apparatus includes a catheter that is directed through the working channel of the duodenoscope and the sphincter of Oddi into the biliary tree. The catheter includes first, second and third lumens with the first lumen being larger than either the second or third lumens and the lumens generally extending between proximal and distal portions of the catheter along parallel axes. Apparatus for cutting the sphincter of Oddi includes a cutting wire extending through the second lumen and externally of the catheter means through a distal port along a length that is coextensive with part of said distal portion of the catheter. A handle attaches to the catheter into the proximal wire portion to control the position and orientation of the cutting wire. The proximal port of the third lumen connects to a contrast agent source and the third lumen delivers contrast agent into the biliary tree through a distal port in the distal end of the catheter.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
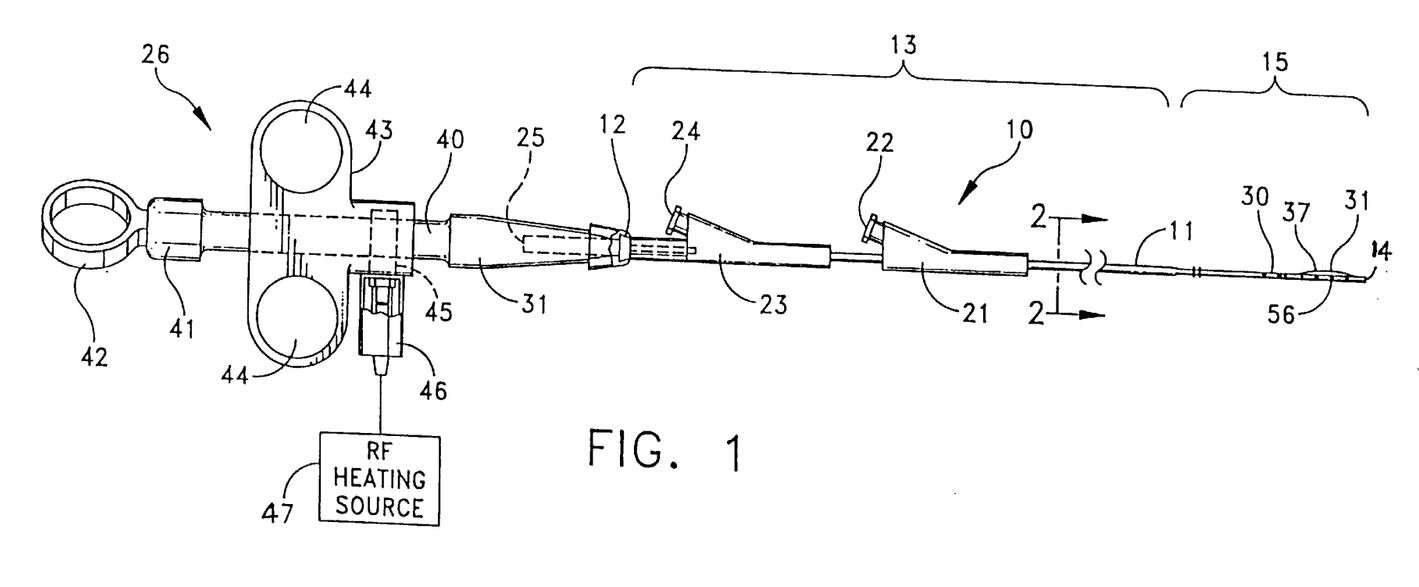
FIG. 1 is a plan view of one embodiment of apparatus constructed in accordance with this invention.

FIG. 1 depicts a catheter apparatus 10 that has the capability of injecting a contrast agent into the biliary tree, of performing a sphincterotomy and of dislodging a gallstone into the duodenum. The apparatus 10 includes a catheter 11 which, for purposes of definition, includes a proximal end portion 12 extending from a proximal end 13 and a distal end 14 with a distal portion 15 extending a short distance from the distal end 14. In a typical application, the catheter will have a working length of 200 cm and the distal end portion 15 will have a length of 6 cm to 9 cm. Normally the distal portion 15 will have a diameter that is smaller than the diameter of the proximal portion to increase the flexibility of the distal portion 15. The reduction in diameter also makes the tip less traumatic and allows the tip portion to reach smaller passages while allowing the larger proximal portion to provide necessary hoop strength and rigidity, particularly where the proximal portion 13 is coextensive with the working channel of a duodenoscope. For example, the proximal and distal portions might have diameters corresponding to 7 Fr and 5.5 Fr catheter sizes (i.e., 0.09" and 0.07" respectively).

Figure 2:
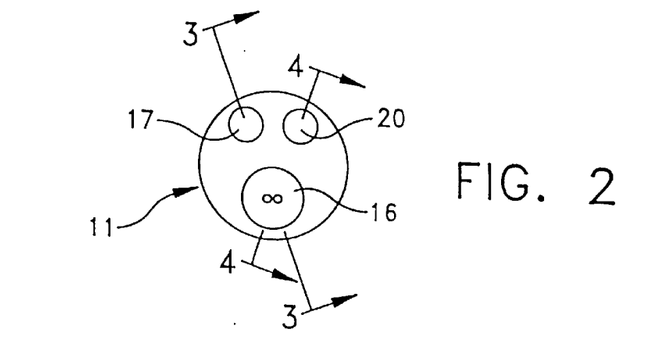
FIG. 2 is a cross-section taken along lines 2—2 in FIG. 1.

As shown particularly in FIG. 2, the catheter 11 has three lumens. A first lumen 16 has a diameter that is greater than either a second lumen 17 or a third lumen 20. In one particular embodiment the lumen 16 has a diameter of 0.040" in the proximal portion 13 that reduces to about 0.037" in the distal portion 15 to receive a standard 0.035" guidewire. In addition the lumen 16 is offset from the center of the catheter 11.

The lumens 17 and 20 are each smaller in diameter than the lumen 16 and are radially offset from the centerline of the catheter, from each other and from the lumen 16. In one particular embodiment the lumens 17 and 20 each have internal diameters of 0.028" in the proximal portions 13 that reduces to about 0.020" in the distal portion 15. As described later, this lumen 20 carries a cutting wire for performing a sphincterotomy and for allowing the infusion of a contrast agent at reasonable rates. The angular spacing between the lumens 17 and 20 is about 45° and the angular spacing between the first lumen 16 and each of the lumens 17 and 20 each is about 157.5°. In this configuration and with these dimensions the proximal portion 13 readily passes through the working channel of any duodenoscope.

Referring again to FIGS. 1 and 2, each of the lumens 16, 17 and 20 includes an entry port in the proximal portion 13 and an exit port in the distal portion 15. Generally, and as described in more detail later, the first lumen 16 has an exit port through the distal end 14 while the exit ports for the lumens 17 and 20 can be sited at different locations in the distal portion 15 depending upon a particular application.

In FIG. 1, the entry ports in proximal portion 13 adjacent the proximal end 12 include an entry port 21 that provides access to the lumen 16 and includes an optional Leur lock fitting 22. A proximally positioned entry port 23 provides access to the lumen 17 and includes an optional Leur lock fitting 24. A proximal entry port 25 for the lumen 20 is located coextensively with a portion of a handle 26 attached to the proximal end 12.

Figure 3:
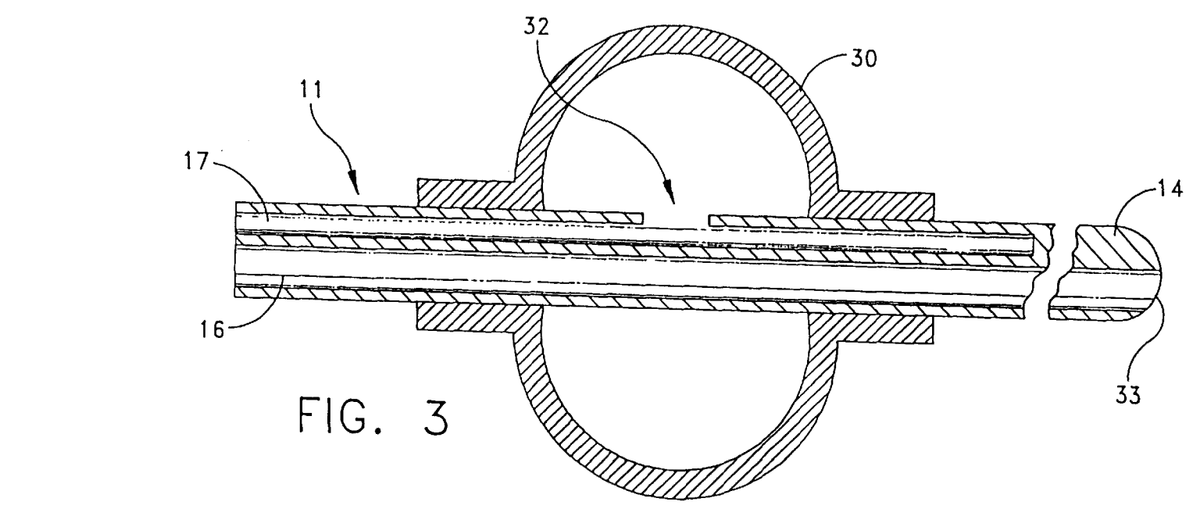
FIG. 3 is a cross-section taken along lines 3—3 in FIG. 2.

Referring to the distal end portion 15, the catheter 11 in this particular embodiment carries an expansible balloon 30 proximally of the excursion of a cutting wire 31 externally of the catheter 11. As shown in FIG. 3, the lumen 17 emerges at a distal exit port 32 through the side of the catheter 11 with the interior of the expansible balloon 30. An extension of the lumen 17 beyond the distal port 32 is sealed by known methods of manufacture. Consequently, fluid forced through the entrance port 23, as by a syringe (not shown) attached to the Leur lock fitting 24, expands the balloon 30 into an occluding orientation as shown in FIG. 3 with an inflated diameter in the range up to 20 mm.

Figure 4:
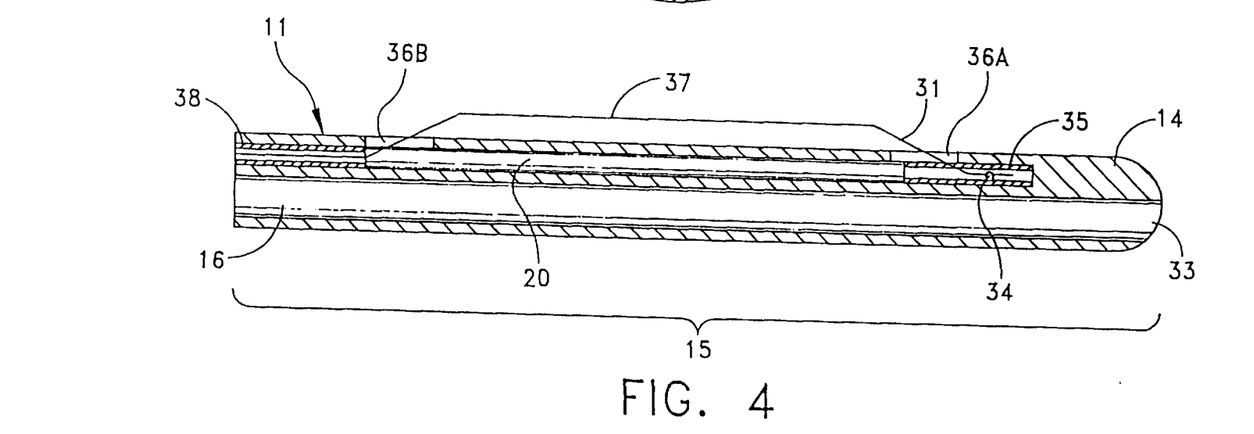
FIG. 4 is a cross-section taken along lines 4—4 in FIG. 2.

As will also be apparent from viewing FIGS. 3 and 4, the first lumen 16 extends through the catheter 11 and terminates with an exit port 33 in the distal end 14. Thus the lumen 16 is adapted for receiving a guidewire through the entrance port 21 that will extend through the catheter 11 and exit the distal end 14 and allow the catheter to slide over that guidewire.

Referring to FIG. 4, a distal end 34 of the cutting wire 31 attaches to a clamp 35 formed at the distal end of the lumen 20. Spaced skived ports 36A and 36B allow an active portion 37 of the cutting wire 31 to emerge from the catheter 11 through the skived aperture 36A, parallel the catheter 11 exteriorly thereof and return into the lumen 20 through the port 36B and a reinforcing sleeve 38. The cutting wire 31 then extends through the lumen 20 to the handle 26 shown in FIG. 1 where it emerges as a proximal end portion 40.

The handle 26, as shown in FIG. 1, includes a central member 41 terminating with a thumb ring 42. The central member 41 extends through and slides with respect to a body section 43 having opposed finger rings 44. The central member 41 also attaches to the catheter 11, and is therefore an extension of the catheter 11. The member 43 additionally includes an internal connector 45 for clamping the proximal end 40 of the cutting wire 31. Thus, when the body 43 is at its distal position as shown in FIG. 1, the distal portion of the catheter 15 is in essentially straight line as shown in FIG. 1 with the active portion 37 of the cutting wire 31 being closely adjacent the catheter 11. Retracting the body portion 43, causes the cutting wire 31 to bend the distal end upwardly as shown in FIG. 1 to a position that is essentially at right angles to the main axis of the catheter, as will be shown later.

The connector block 45 and the cutting wire 31 are generally conductive members that attach through an RF connector 46 to an RF heating source 47. The use of such RF heating sources 47 for energizing a cutting wire 31 thereby to cut the sphincter muscle is well known in the art and represents one possible sphincterotomy procedure that can be adapted for the apparatus of this invention and is not described further.

Figure 5:
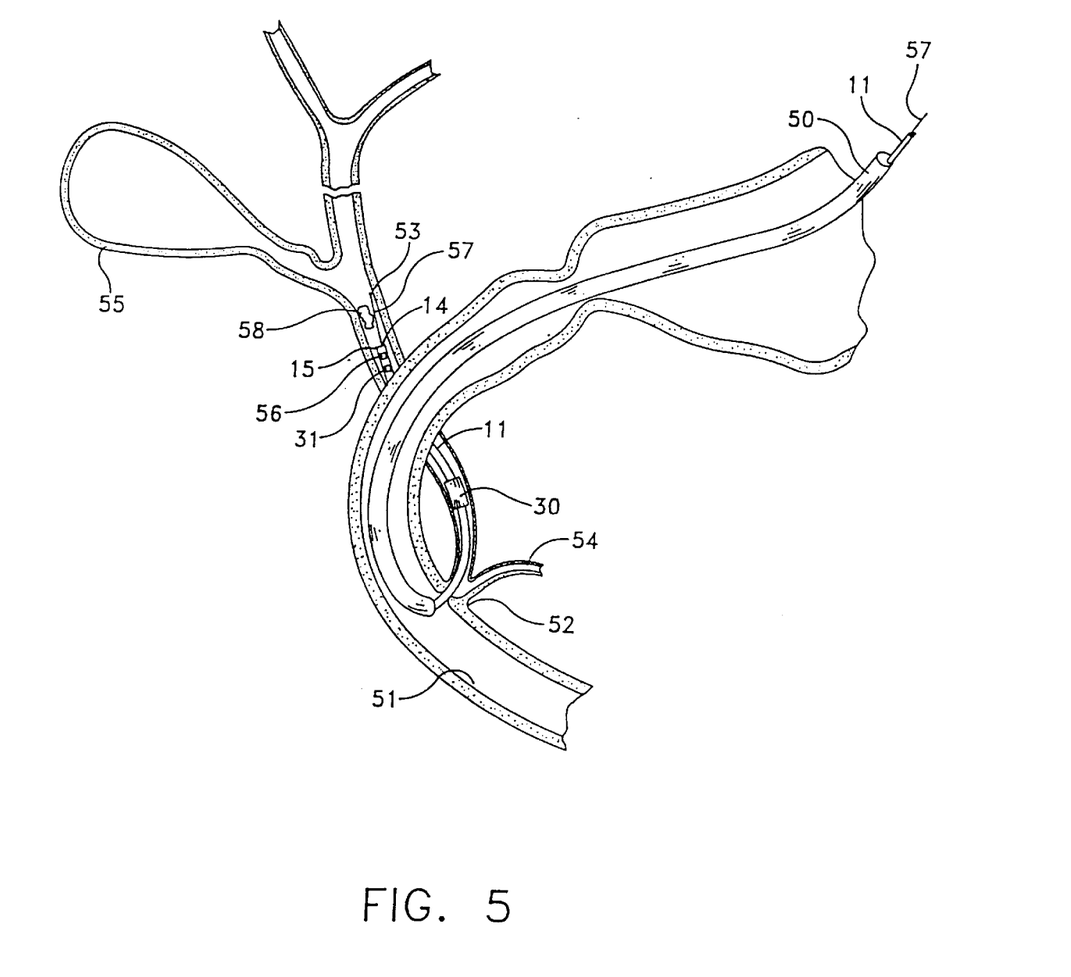
FIG. 5 depicts the apparatus of FIG. 1 positioned through a duodenoscope for injecting contrast agent into the biliary tree.

With this description of the apparatus structure, it will now be possible to understand its use in a particular application. FIG. 5 discloses, in a partially broken and schematic view, the positioning of a duodenoscope 50 in the duodenum 51 adjacent the sphincter of Oddi 52. A catheter 11 such as constructed in FIG. 1 passes through the sphincter of Oddi 52 into the common bile duct 53, bypassing the pancreatic duct 54. The distal end 14 does not extend to the gallbladder 55.

Fluoroscopy allows the appropriate positioning by utilizing a series of radio-opaque markers 56 at the distal portion 15 that may include the clamp 35 and the reinforcing sleeve 38 in FIG. 4. The catheter 11 can be positioned with or without the presence of a guidewire 57 in the lumen 16 shown in FIGS. 2, 3 and 4. For purposes of injecting the contrast agent, any guidewire 57 can be withdrawn to allow the contrast agent to be injected through the lumen 16 for purposes of fluoroscopic examination to confirm the presence of one or more gallstones 58. It is also possible during the operation to expand the balloon 30 to occlude the bile duct 53 and block any migration of contrast agent into the duodenum 51 or the pancreatic duct 54.

Figure 6:
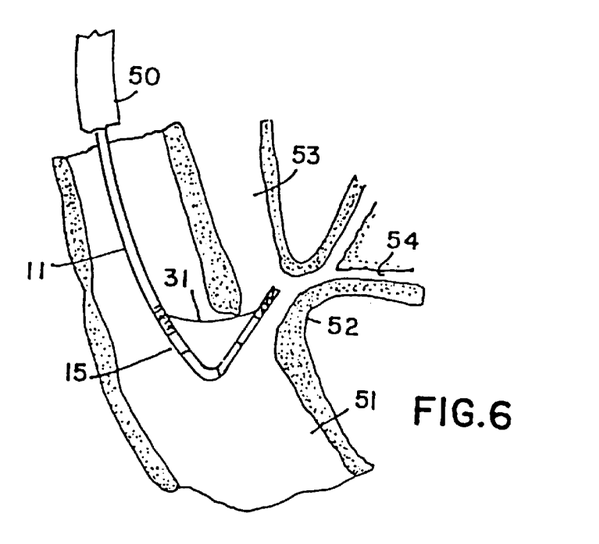
FIG. 6 is an enlarged view that depicts the orientation of the apparatus in FIG. 1 for performing a sphincterotomy.

FIG. 6 is an enlarged view showing the duodenum 51, sphincter of Oddi 52, portions of the pancreatic duct 54 and the common bile duct 53. In FIG. 6 the catheter 11 has been positioned relative to the duodenoscope 50 through the opening of the sphincter of Oddi 52. The handle 43 in FIG. 1 has been drawn proximally to deflect the distal portion 15 into essentially a right angle configuration such that the cutting wire 31 abuts a portion of the sphincter of Oddi 52. The application of RF heating to the cutting wire 31 then will cut the sphincter of Oddi 52 and enlarge the opening therethrough. As will be apparent, the sphincterotomy is performed with direct visualization of the sphincter of Oddi through the duodenoscope.

Moreover, as has been observed by others, catheters having guidewire and cutting wire lumens tend to assume a particular angular orientation when the distal portion 15 emerges from the duodenoscope. This orientation is essentially independent of the angular position of the catheter when it is inserted into the duodenoscope. The offset nature of the lumen 20 as shown in FIG. 2, improves the location of the cutting wire 31 as the distal portion 15 passes through the sphincter of Oddi 52. Specifically the angularly offset brings the cutting wire 31 into better alignment with the common bile duct 53 and displaces the cutting wire from the pancreatic duct 54.

Figure 7:
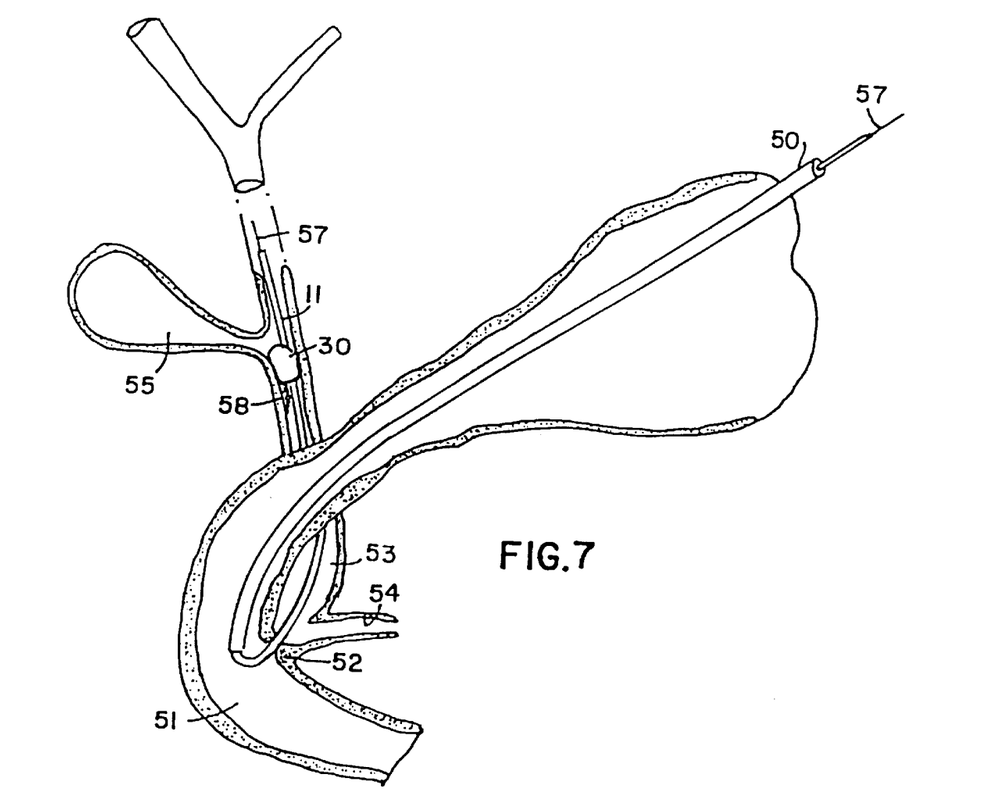
FIG. 7 depicts the apparatus of FIG. 1 positioned through a duodenoscope for dislodging material within the common bile duct.

FIG. 7 depicts the catheter after the sphincterotomy and after the catheter 11 is advanced over the guidewire 57, if used. FIG. 7 also discloses the catheter 11 after the balloon 30 has been moved beyond a gallstone 58 in the bile duct 53.

The balloon 30 is expanded so that upon withdrawal of the catheter 11 the balloon 30 will dislodge the gallstones 57 and sweep them through the sphincter of Oddi 52 into the duodenum 51.

As will now be apparent from the description of the particular catheter apparatus 10 shown in FIG. 1 and its use as discussed with respect to FIGS. 5, 6, and 7, the single catheter apparatus of this invention is capable of providing diagnostic contrast agent injection, of performing a sphincterotomy and of dislodging gallstones in the common bile duct or other portions of the biliary tree without having to exchange a catheter. Moreover, positioning and sizing of the lumens enables these functions to be performed with a catheter apparatus that is readily adapted for use in the working channels of standard duodenoscopes. Consequently the gallstones can be removed from the biliary tree without bile duct incisions and accompanying surgical procedures, as duodenoscope can be introduced through the alimentary tract. Consequently the entire procedure is adapted for being performed more rapidly than prior art procedures and with fewer components. The net effect is to reduce patient trauma and the overall time and cost of conducting the procedure.

Figure 8:
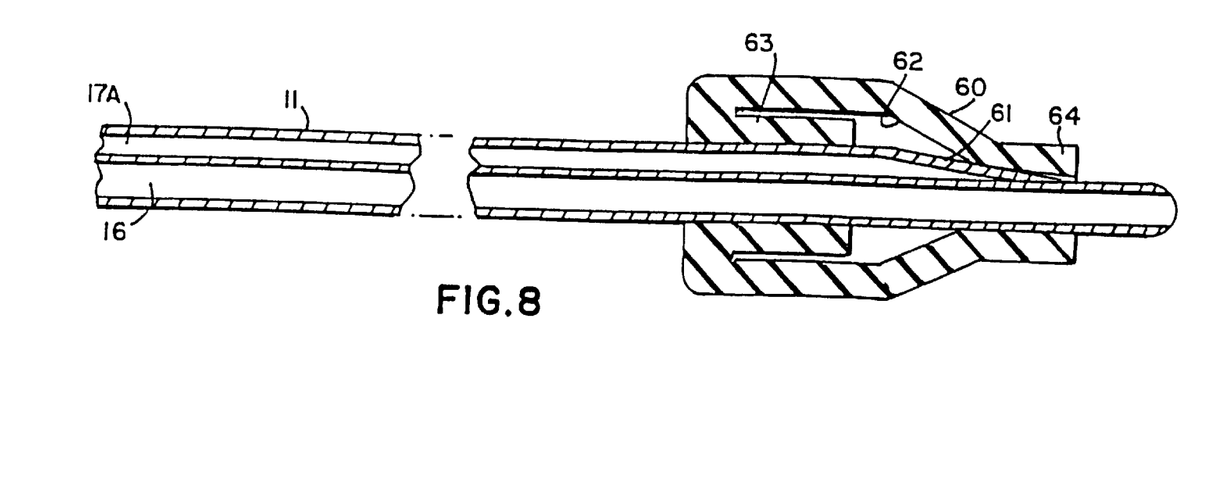
FIG. 8 is a cross-section of an alternative embodiment of the apparatus as viewed generally along lines 3—3 in FIG. 2.

In FIG. 1 the balloon 30 is located proximally of the cutting wire 31. FIG. 8 discloses an alternative embodiment in which a balloon 60 is located distally of the cutting wire 31. More specifically, the distal end of a lumen 17A, corresponding to the lumen 17 in FIGS. 3 and 4, is sealed. A side facing exit port 61 skived or otherwise formed in the catheter 11 opens into a chamber 62 formed by the balloon 60. A first sealing portion 63 and a sealing portion 64 of the balloon 60 connect proximally and distally of the aperture 61 respectively and seal the chamber 62.

Introduction of a balloon inflation fluid through the lumen 17A expands the balloon 60 into an occluding orientation corresponding to the orientation of the balloon 30 shown in FIG. 3. Retraction of the catheter 11 with the distal balloon 60 inflated enables withdrawal of a gallstone from the bile duct. This particular embodiment is particularly adapted when it is determined that a gallstone is located high in the biliary tree to minimize the incursion of the distal portion 15 through the biliary tree beyond the gallstone or in any application in which the internist desires to minimize the length of the distal portion 15 that extends beyond the occluding balloon.

Figure 9:
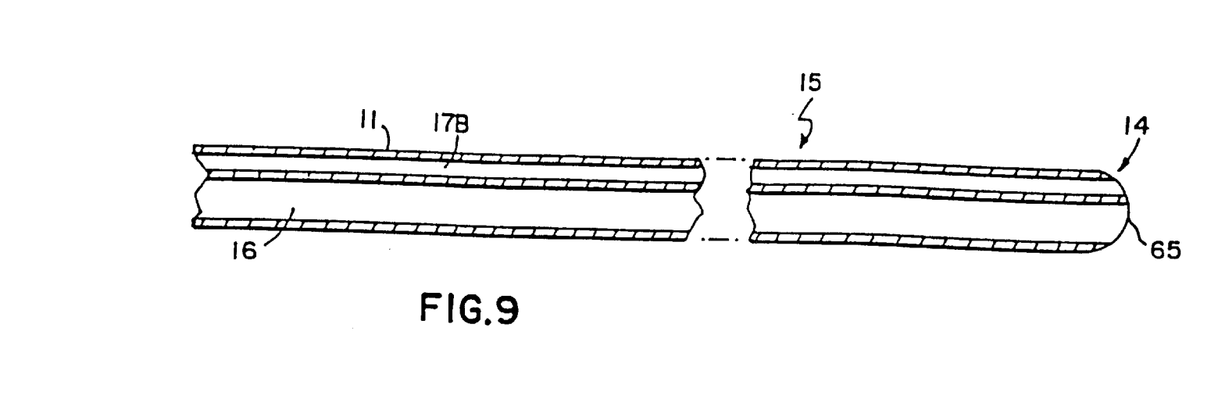
FIG. 9 is a cross-section of still another embodiment of this invention taken along lines 3—3 in FIG. 2.

FIG. 9 discloses another embodiment of this invention for enlarging the sphincter of Oddi and performing another procedure, such as injecting a contrast agent into the biliary tree, as might be used in the diagnosis and treatment of a stricture in the biliary tree. In this particular embodiment an exit port 65 from the lumen 17B is located in the distal end 14 of the distal portion 15. The lumen 16 then can be used for a guidewire and the lumen 17B, for injecting the contrast agent directly into the biliary tree while the guidewire remains in place. The apparatus would then be positioned to perform a sphincterotomy without having to exchange a catheter should the procedure be warranted.

As still another alternative, the internist could utilize a conventional catheter for purposes of injecting the contrast agent to determine the need for gallstone removal. If treatment were indicated, the internist could then utilize apparatus as shown in FIG. 1 with a single exchange over the guidewire that would pass through the lumen 16 as previously described.

Therefore, it will now be apparent that apparatus constructed in accordance with this invention attains the several objects and the advantages of this invention. More particularly, catheter apparatus constructed in accordance with this invention allows the injection of a contrast agent, the performance of a sphincterotomy and dislodging gallstones from the common bile duct through the enlarged sphincter of Oddi into the duodenum all without requiring any catheter exchanges. Moreover, this apparatus allows such a procedure to occur through a duodenoscope to minimize patient trauma. The use of a single catheter with an elimination of catheter exchanges further reduces the time and costs associated with the use of multiple, single-function catheter devices.

As will be apparent from the foregoing description, many alterations can be made to the specifically disclosed embodiments. Different balloon structures can be used and located at alternative positions. Different cutting wire embodiments and orientations can be used. Thus, although this invention has been disclosed in terms of certain embodiments, it will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An apparatus for treating a patient, the apparatus comprising:

a catheter having a proximal end and a distal end, the catheter including first, second, and third lumens extending therethrough from the proximal end to the distal end, the second and third lumens each including an entry port at the proximal end in communication with an exit port at the distal end;

an actuator connected to the proximal end of the catheter;

a first device at the distal end proximate the exit port of the second lumen for performing a first operation on a patient; and a second device at the distal end proximate the exit port of the third lumen for performing a second operation on a patient, the second device extending through the third lumen to connect to the actuator so that actuation of the actuator causes the second device to perform the second operation.

2. The apparatus of claim 1, wherein the first device is expansible.

3. The apparatus of claim 1, wherein the first device is an expansible balloon.

4. The apparatus of claim 3, wherein the entry port of the second lumen is adapted to receive fluid for expanding the expansible balloon.

5. The apparatus of claim 3, wherein the first operation includes retrieval of objects from within the patient.

6. The apparatus of claim 1, wherein the second device is a cutting device.

7. The apparatus of claim 6, wherein the cutting device connects to the distal end of the third lumen, and a portion of the cutting device is exterior the third lumen.

8. The apparatus of claim 7, wherein the second operation includes cutting tissue from the patient to enlarge a working area within the patient.

9. The apparatus of claim 7, wherein the cutting device is a cutting wire.

10. The apparatus of claim 9, wherein the actuator includes a connector connected to the cutting wire for connection to a heating source.

11. The apparatus of claim 1, wherein the entry port of the third lumen is adapted to receive fluid for discharge from the exit port of the third lumen.

12. The apparatus of claim 1, wherein the first lumen has a diameter larger than a diameter of either the second lumen or the third lumen.

13. The apparatus of claim 12, wherein the first lumen is adapted to receive a guide wire.

14. The apparatus of claim 1, wherein the first device is expansible and the second device is a cutting device.

15. An apparatus for removal of objects from a biliary tree of a patient, the apparatus comprising:

a catheter for being directed through a sphincter of Oddi and into a biliary tree, the catheter having a proximal end and a distal end, the catheter including first, second, and third lumens extending therethrough from the proximal end to the distal end, the second and third lumens each including an entry port at the proximal end in communication with an exit port at the distal end;

an actuator connected to the proximal end of the catheter;

a first device at the distal end proximate the exit port of the second lumen for performing an operation on a patient; and a cutting device at the distal end proximate the exit port of the third lumen, the cutting device extending through the third lumen to connect to the actuator so that actuation of the actuator causes the cutting device to cut a sphincter of Oddi.

16. The apparatus of claim 15, wherein the first device is expansible.

17. The apparatus of claim 15, wherein the first device is an expansible balloon.

18. The apparatus of claim 17, wherein the entry port of the second lumen is adapted to receive fluid for expanding the expansible balloon.

19. The apparatus of claim 17, wherein the operation includes retrieval of objects from within a patient.

20. The apparatus of claim 15, wherein the cutting device connects to the distal end of the third lumen, and a portion of the cutting device is exterior the third lumen.

21. The apparatus of claim 20, wherein the cutting device is a cutting wire.

22. The apparatus of claim 21, wherein the actuator includes a connector connected to the cutting wire for connection to a heating source.

23. The apparatus of claim 15, wherein the entry port of the third lumen is adapted to receive fluid for discharge from the exit port of the third lumen.

24. The apparatus of claim 15, wherein the first lumen has a diameter larger than a diameter of either the second lumen or the third lumen.

25. The apparatus of claim 24, wherein the first lumen is adapted to receive a guide wire.

26. A method of removing objects from the biliary tree of a patient, the method comprising the steps of:

inserting a catheter into a patient, the catheter having first, second, and third lumens extending therethrough from a distal end within a patient to a proximal end exterior a patient, the second and third lumens each including an entry port at the proximal end, cutting a sphincter of Oddi with a cutting device to enlarge a working area within a patient, the cutting device extending through the third lumen to the distal end, expanding a device located beyond an object in a biliary tree, the device being connected to the catheter at the distal end proximate the exit port of the second lumen, and withdrawing the catheter from a patient while the device is expanded to remove an object from a biliary tree.

27. The method of claim 26, further comprising the step of positioning the catheter through fluoroscopy.

28. The method of claim 27, wherein the catheter includes markers at the distal end.

29. The method of claim 26, further comprising the step of injecting a contrast agent through the third lumen to confirm the presence of an object.

30. The method of claim 29, wherein the device is expanded during the injecting step to block migration of a contrast agent.

31. The method of claim 26, wherein the cutting device is a cutting wire, a portion of the cutting wire being exterior to the third lumen.

32. The method of claim 31, wherein heat is applied to the cutting wire to cut the sphincter of Oddi.

33. The method of claim 26, wherein the device is an expansible balloon, and the expanding step includes inserting fluid through the second lumen and to the exit port of the second lumen to expand the expansible balloon.

34. The method of claim 26, wherein the first lumen has a diameter larger than a diameter of either the second lumen or the third lumen.

35. The method of claim 34, further comprising positioning the catheter within a patient by use of a guidewire in the first lumen.

* * * * *